(12) United States Patent
Shalaby et al.

(10) Patent No.: US 7,842,749 B2
(45) Date of Patent: Nov. 30, 2010

(54) TISSUE PROTECTING SPRAY-ON COPOLYMERIC FILM COMPOSITION

(75) Inventors: Shalaby W. Shalaby, Anderson, SC (US); James M. Lindsey, III, Pendleton, SC (US)

(73) Assignee: Poly-Med, Inc., Anderson, SC (US)

( * ) Notice: Subject to any disclaimer, the term of this patent is extended or adjusted under 35 U.S.C. 154(b) by 931 days.

(21) Appl. No.: 11/175,636

(22) Filed: Jul. 5, 2005

(65) Prior Publication Data

US 2006/0025516 A1 Feb. 2, 2006

Related U.S. Application Data

(60) Provisional application No. 60/598,343, filed on Aug. 2, 2004.

(51) Int. Cl.
*C08L 31/00* (2006.01)
(52) U.S. Cl. ............... 524/556; 526/264; 526/319; 526/303.1
(58) Field of Classification Search ............ 524/556; 526/264, 319, 303.1
See application file for complete search history.

(56) References Cited

U.S. PATENT DOCUMENTS

| | | | |
|---|---|---|---|
| 3,577,516 A * | 5/1971 | Gould et al. ............ 424/46 |
| 3,577,526 A * | 5/1971 | Gould et al. ............ 424/232.1 |
| 4,057,623 A * | 11/1977 | Hase et al. ............ 514/772.5 |
| 4,291,025 A | 9/1981 | Pellico |
| 4,303,066 A | 12/1981 | D'Andrea |
| 4,318,746 A | 3/1982 | Claffey et al. |
| 4,393,048 A | 7/1983 | Mason, Jr. et al. |
| 4,569,784 A | 2/1986 | Moore |
| 4,650,817 A | 3/1987 | Allen, Jr. et al. |
| 4,987,893 A | 1/1991 | Salamone et al. |
| 5,330,746 A * | 7/1994 | Friedman et al. ............ 424/49 |
| 5,464,154 A * | 11/1995 | Nielsen ............ 239/1 |
| 6,231,875 B1 * | 5/2001 | Sun et al. ............ 424/401 |
| 7,019,067 B2 * | 3/2006 | Holguin et al. ............ 524/558 |
| 7,276,574 B2 * | 10/2007 | Hirota et al. ............ 528/482 |
| 2003/0100694 A1 | 5/2003 | Holguin |
| 2003/0135195 A1 * | 7/2003 | Jimenez et al. ............ 604/500 |
| 2004/0071871 A1 * | 4/2004 | Queval et al. ............ 427/207.1 |
| 2004/0266965 A1 * | 12/2004 | Holguin et al. ............ 526/320 |
| 2005/0014912 A1 * | 1/2005 | Hirota et al. ............ 526/90 |

FOREIGN PATENT DOCUMENTS

EP 1541592 A1 * 6/2005

OTHER PUBLICATIONS

Hadjichristidis et al. Block copolymers, John Wiley & Sons, Inc., 2003, Chapter 3, pp. 47-64.*
Hadjichristidis et al. Block copolymers, John Wiley & Sons, Inc., 2003, Chapter 3, pp. 47-64.*
Brodovsky, S., et al., J. Dermatol. Surg. Oncol., 12(4), 386-387 (1986).

* cited by examiner

*Primary Examiner*—David Wu
*Assistant Examiner*—Michael M Bernshteyn
(74) *Attorney, Agent, or Firm*—Leigh P. Gregory

(57) ABSTRACT

This invention deals with a tissue protecting, spray-on film composition comprising an amphiphilic film-forming, segmented/block copolymer derived form at least one water-soluble monomer and at least another water-insoluble monomer, wherein the film can be formed from a water soluble organic solvent such as 2-propanol, acetone, and ethyl acetate. The film can contain a bioactive agent including those to have antimicrobial, anesthetic, anti-inflammatory, and wound-healing activities.

12 Claims, No Drawings

US 7,842,749 B2

TISSUE PROTECTING SPRAY-ON COPOLYMERIC FILM COMPOSITION

The present application claims the benefit of prior provisional application, U.S. Ser. No. 60/598,343, filed Aug. 2, 2004.

FIELD OF THE INVENTION

This invention deals with amphiphilic, copolymeric, sprayable, organic solvent-borne compositions so designed to provide a means to yield a medicated or unmedicated elastomeric, thin film on intact or compromised vertebrate animal tissue to protect against damaging environmental elements, aid in healing, and/or deliver needed medicaments. The physical and biomechanical properties of these compositions are due to special chain design of the constituent copolymers wherein said chains comprise highly hydrophilic as well as highly hydrophobic segments or blocks.

BACKGROUND OF THE INVENTION

Protecting compromised tissues, as in the case of lacerated skin or mucous membrane, has been of interest to clinicians for decades. This commenced by using the now-described "traditional bandage." This was followed by the development of adhering, highly conformable, thin film, such as Opsite Flexigrid® (marketed by Smith & Nephew) and similar systems later on. The Opsite Flexigrid® consists of a thin polyurethane membrane coated with a layer of an acrylic adhesive. The dressing, which is permeable to both water vapor and oxygen, is impermeable to micro-organisms. Once in position, the film provides an effective barrier to external contamination, while producing a moist environment at the surface of the wound by reducing water vapor loss from the exposed tissue. Under these conditions in shallow wounds, scab formation is prevented and epidermal regeneration takes place at an enhanced rate, compared with that which occurs in wounds treated with traditional dry dressings. The polyurethane film is supported on a removable flexible carrier that can be drawn upon to provide a record of the size and shape of the wound to which the dressing is applied. Opsite Flexigrid® was recommended by the manufacturer for use in the treatment of scalds, first- or second-degree burns, donor sites, post-operative wounds, minor injuries (including abrasions and lacerations), and for the prevention and treatment of superficial pressure areas. Larger sizes of the dressing without the flexible carrier are marketed as incise drapes. Concomitant with the development of Opsite and similar films, a few investigators pursued the development of the so-called liquid bandages as discussed in the following paragraphs.

Naturally occurring and derivatized naturally occurring polymers have been tested as liquid adhesive coatings for bandage applications and, in some cases, utilized commercially. Typical examples are nitrocellulose in various solvents (e.g., New Skin-Medtech Laboratories, Inc., Cody, Wyo.), agar in water and diethylene glycol (U.S. Pat. No. 4,291,025), carrageenan and hydroxypropylmethyl cellulose in water (U.S. Pat. No. 4,318,746), and alginate in glycerin (U.S. Pat. No. 4,393,048). All of these natural polymers can support microbial growth, hence requiring the addition of a preservative or antimicrobial agent to the product. The liquid bandages based on water, diethylene glycol, glycerin, etc., are not only susceptible to microbial growth, but are often also slow drying due to high heats of vaporization; and are often water sensitive, which can result in problems when used on areas of the body exposed to water. One commercial product, New Skin, does dry rapidly and is not water sensitive, but can cause stinging and further irritation of the skin upon application.

A few synthetic polymers have been patented for use as liquid adhesive coatings for bandage applications, most notably polymers containing 2-hydroxyethyl methacrylate (U.S. Pat. No. 4,303,066). These bandages based on the use of solvents can sting abraded areas; and the films can swell and wash off when in contact with water. U.S. Pat. No. 4,569,784 claims an ointment, not a long-lasting bandage composed of an emulsion of water and silicone fluids, among other fluids. This reference can provide for an immediate soothing, but often not long-lasting, treatment of the skin or mucous membranes. It also does not provide for fast drying, abrasion resistance, and other attributes which a polymer film can provide.

Additionally, traditional wound and surgical bandages, such as Band-Aids (Johnson & Johnson, New Brunswick, N.J.), comprised of film backings with adhesive, may contain silicones as part of either the adhesive or the backing (e.g., U.S. Pat. No. 4,650,817). These products are not applied as liquid adhesive coating where films form and adhere directly on the skin. This led Salamone et al., (U.S. Pat. No. 4,987,893) to develop a liquid polymer-containing coating material which can act as a bandage or dressing to protect wounds, when applied in liquid form and air-dried on the wound to form an adherent, solid protective film without significant stinging to the skin or mucous membranes of the user. The liquid polymer-containing coating material of U.S. Pat. No. 4,987,893 was noted to consist essentially of a siloxane-containing polymer and a solvent system comprising a polar solvent in small amount and a volatile liquid which is non-stinging to a user but provides bulk and formability to the liquid. Preferably, the polymer is present from 1 to 40% by weight, the volatile liquid from 59.9 to 98.9% by weight and the polar solvent from 0.1 to 10% by weight. When the polar solvent is eliminated, the volatile liquid can be in amounts of 60 to 99%. The solvent is minimized to obtain flowability desired at the lowest solvent level feasible which minimizes stinging. The material forms a coating or bandage in the form of a dried film when applied to a surface or the skin of a user.

Collectively, U.S. Pat. No. 4,987,893 claims that combinations of alky siloxy siloxane-containing polymers admixed with liquid polydimethylsiloxanes are excellent non-stinging, non-irritating liquid coating material for forming films which act as conformable bandages adhering to and protecting nails, skin, and mucous membrane wounds from abrasion, contamination, and desiccation, while stopping pain from exposed nerve ends and allowing body fluid evaporation.

However to those skilled in the art of polymers, the compositions of U.S. Pat. No. 4,987,893 are (1) expected to result in low tear strength films because of being made of polysiloxane-based chains; (2) not expected to form, in a timely manner, a solid film at the application site because of the low volatility of their major constituents; (3) expected to yield hydrophobic films that have low or no tendency to adhere to moist tissue for sufficient periods of time—these films offer no advantage over regular bandages; and (4) not expected to yield thin film on difficult-to-reach areas. Such undesirable features of U.S. Pat. No. 4,987,893, and the prior art that preceded this patent provided a strong incentive to explore the development of the amphiphilic, water-insoluble spray-on liquid compositions subject of this invention which have been noted to represent a series of preferred medicated and unmedicated alternatives to regular bandages and all so-called liquid bandages of the prior art. A special incentive to explore the development of certain segments of the present invention dealing with pain-free, film-forming compositions was related to the effective use of Nobecutane spray as a temporary dressing of skin graft donor sites [Brodovsky, S., et al., *J. Dermatol. Surg. Oncol.*, 12(4), 386 (1986)] in spite of using the stingy ethyl acetate as solvent. The respective clinicians noted that various methods have been used for managing split-thickness skin graft donor sites. Open and closed techniques have been suggested by various authors with the purpose of achieving smooth and rapid healing of the wound. There is growing evidence to suggest that the site and quality of the healing is improved when the wound is protected from dehydration and further mechanical trauma. A recent method is the spraying of Nobecutane Spray on the donor site. Nobecutane sprayed on a wound forms a plastic film which serves as a dressing material. It contains specially modified acrylic resin in an organic solvent (ethyl acetate) and TMTD (tetramethylthiuram disulphide) which is strongly bactericidal and fungicidal. This method was used on 50 patients and found to be effective in achieving rapid and painless healing. The dressing is transparent, permits easy follow-up of healing in the donor site, protects the wound against infection, and does not inconvenience the patient. The treatment is simple, economical, and does not require special skills. The dressing peels off spontaneously after epidermal regeneration of the wound is completed. No complications or allergic reaction were observed with this treatment.

A commercial spray bandage sold under the trade name Curad® Spray Bandage (Beiersdorf, Inc., Winton, Conn.) was described to have the following ingredients: poly(methyl acrylate-isobutene-mono-isopropyl maleate), ethyl acetate, menthol, pentane, and carbon dioxide. It was noted to yield a transparent, breatheable film that seals applications site from water, dirt, and germs for maximum protection. A second bandage spray that is water-soluble is commercialized by Swift First Aid as Swift Bandage Spray. It is advertised to provide an invisible coat for protection from dire, dust, and bacteria. It has been recommended for minor injuries, irritations, and insect bites. The inactive ingredients of the spray-on are ethyl alcohol, isobutane, n-butane, propane, a water-soluble copolymer of N-vinyl pyrrolidone, and vinyl acetate. The spray-on also contains benzethonium chloride (0.2% w/w) and benzocaine (5% w/w) as active ingredients. Unfortunately, this coating is not expected to reside for a practically effective period of time at the application site because of its water solubility.

None of the cited prior art has described or made obvious the conception of the spray-on compositions of the amphiphilic, non-water-soluble, segmented/block copolymers that are capable of yielding conformable, high compliance film with modulated oxygen permeability and water vapor transmission which are the subject of the present invention.

SUMMARY OF THE INVENTION

This invention deals generally with a tissue protecting, spray-on film composition comprising an amphiphilic film-forming, segmented/block copolymer derived from at least one water-soluble monomer and at least another water-insoluble monomer, wherein said respective film can be formed from a water soluble organic solvent such as 2-propanol, acetone, and ethyl acetate. The film can contain a bioactive agent including those to have antimicrobial, anesthetic, anti-inflammatory, and wound-healing activities.

One primary aspect of this invention deals with a tissue protecting spray-on film composition comprising an amphiphilic, film-forming, segmented/block copolymer having a molecular weight of at least 15 kDa derived from at least one water-insoluble alkyl methacrylate and at least one water-soluble monomer selected from the group consisting of N-vinyl pyrrolidone, acrylamide, N-methyl acrylamide, 2-hydroxyethyl methacrylate wherein said copolymer is soluble in one or more water soluble solvent selected from the group represented by ethyl acetate, ethanol, 2-propanol, and acetone, wherein (1) the said solvent may contain water at more than 0.1 percent of its volume; (2) the segmented/block copolymer may be derived from n-hexyl methacrylate and N-vinyl pyrrolidone; and (3) the segmented/block copolymer may be prepared by the controlled incremental addition of either or both monomers (comonomers) to the polymerization reaction mixture under typical (or traditional) free-radical conditions. An alternative method for preparing the segmented/block copolymer subject of this invention comprises solution or bulk polymerization through controlled/living radical polymerization (CLRP) using $NiBr_2 (PPh_3)_2$ as a catalyst and ethyl 2-bromobutyrate as an initiator.

A specific aspect of this invention deals with a tissue protecting spray-on film composition comprising an amphiphilic, film-forming, segmented/block copolymer, having a molecular weight of at least 15 kDa, derived from n-hexyl methacrylate and one or more monomer selected from the group represented by N-vinyl pyrrolidone and 2-hydroxy ethyl methacrylate, acrylamide, and N-methyl acrylamide.

A general aspect of this invention addresses a tissue protecting spray-on film composition comprising an amphiphilic, film-forming, segmented/block copolymer having a molecular weight of at least 15 kDa derived from at least one water-insoluble alkyl methacrylate and at least one water-soluble monomer selected from the group consisting of N-vinyl pyrrolidone, acrylamide, N-methyl acrylamide, 2-hydroxyethyl methacrylate wherein said copolymer is soluble in one or more water soluble solvent selected from the group represented by ethyl acetate, ethanol, 2-propanol, and acetone, wherein the said copolymer is made following a tellurium mediated living radical polymerization (TeRP) using one or more organotellurium compound selected from the group represented by $Ph(CH_3)CH-Te-CH_3$, $PHCH_2-TeMe$, $Ph-CH(CH_3)-Te-CH_3$, and $(CH_3)_2C(COOEt)-Te-CH_3$, wherein Ph=phenyl group and Me=methyl group, and preferably the copolymerization entails the use of dimethyl ditelluride.

Another general aspect of this invention pertains to a tissue protecting spray-on film composition comprising an amphiphilic, film-forming, segmented/block copolymer having a molecular weight of at least 15 kDa derived from at least one water-insoluble alkyl methacrylate and at least one water-soluble monomer selected from the group consisting of N-vinyl pyrrolidone, acrylamide, N-methyl acrylamide, 2-hydroxyethyl methacrylate wherein said copolymer is soluble in one or more water soluble solvent selected from the group represented by ethyl acetate, ethanol, 2-propanol, and acetone, wherein said copolymer comprises an A-B diblock chain structure wherein the A-block is derived from n-hexyl methacrylate and the B-block is derived from a monomer selected from the group represented by N-vinyl pyrrolidone, 2-hydroxyl ethyl methacrylate, acrylamide, and N-methyl acrylamide. Alternatively, the copolymer may be based on an A-B-A triblock chain structure wherein the A-block is derived from a monomer selected from the group represented by N-vinyl pyrrolidone, 2-hydroxyl ethyl methacrylate, acrylamide, and N-methyl acrylamide and the B-block is derived from one or more alkyl methacrylate monomer selected from the group represented by n-hexyl and n-butyl methacrylate or structural isomers thereof. As a second structural alternative, the copolymer may be based on a B-A-B triblock chain structure wherein the A-block is derived from a monomer selected from the group represented by N-vinyl pyrrolidone, 2-hydroxy ethyl methacrylate, acrylamide, and N-methyl acrylamide and the B-block is derived from one or more alkyl methacrylate monomer selected from the group represented by n-hexyl and n-butyl methacrylate, or structural isomers thereof.

Another aspect of this invention pertains to a tissue protecting spray-on film composition comprising an amphiphilic, film-forming, segmented/block copolymer, having a molecular weight of at least 15 kDa, in the form of a breatheable, adhering film for protecting compromised skin, wherein said film displays higher oxygen permeability and lower water vapor transmission compared with a Nylon 6 film control at 25° C. and 37° C., respectively.

Another aspect of this invention deals with a tissue protecting spray-on film composition comprising an amphiphilic, film-forming, segmented/block copolymer having a molecular weight of at least 15 kDa derived from at least one water-insoluble alkyl methacrylate and at least one water-soluble monomer selected from the group consisting of N-vinyl pyrrolidone, acrylamide, N-methyl acrylamide, 2-hydroxyethyl methacrylate wherein said copolymer is soluble in one or more water soluble solvent selected from the group represented by ethyl acetate, ethanol, 2-propanol, and acetone, wherein said film functions as a protective barrier for tissues of the buccal cavity, mandibular tissue, and dental varnish.

Another aspect of this invention deals with a tissue protecting spray-on film composition comprising an amphiphilic, film-forming, segmented/block copolymer having a molecular weight of at least 15 kDa derived from at least one water-insoluble alkyl methacrylate and at least one water-soluble monomer selected from the group consisting of N-vinyl pyrrolidone, acrylamide, N-methyl acrylamide, 2-hydroxyethyl methacrylate wherein said copolymer is soluble in one or more water soluble solvent selected from the group represented by ethyl acetate, ethanol, 2-propanol, and acetone, wherein said composition comprises a UVB light-absorbing sunscreen compound for use as a protective film on skin.

A key aspect of this invention deals with a tissue protecting spray-on film composition comprising an amphiphilic, film-forming, segmented/block copolymer having a molecular weight of at least 15 kDa derived from at least one water-insoluble alkyl methacrylate and at least one water-soluble monomer selected from the group consisting of N-vinyl pyrrolidone, acrylamide, N-methyl acrylamide, 2-hydroxyethyl methacrylate wherein said copolymer is soluble in one or more water soluble solvent selected from the group represented by ethyl acetate, ethanol, 2-propanol, and acetone, wherein said composition comprises an antimicrobial agent selected from the group represented by miconazole and ketoconazole for use in treating athletes' foot and nail infection, and/or a biocompatible dye.

A specific aspect of this invention pertains to a tissue protecting spray-on film composition comprising an amphiphilic, film-forming, segmented/block copolymer having a molecular weight of at least 15 kDa derived from at least one water-insoluble alkyl methacrylate and at least one water-soluble monomer selected from the group consisting of N-vinyl pyrrolidone, acrylamide, N-methyl acrylamide, 2-hydroxyethyl methacrylate wherein said copolymer is soluble in one or more water soluble solvent selected from the group represented by ethyl acetate, ethanol, 2-propanol, and acetone, wherein the said composition is used as a disinfectant spray bandage for depositing a flexible-barrier, solid microfilm onto living tissue as in intact or compromised skin, ulcers, or burns, through the combined processes of gas-propelled spray atomization and solvent evaporation.

Another aspect of this invention deals with a disinfectant spray bandage composition comprising an alcoholic solution of at least 5 percent w/v of at least one amphiphilic, essentially water-insoluble, segmented/block copolymer having a molecular weight of at least 15 kDa, wherein the alcoholic solution comprises a copolymer of an N-vinyl lactam and an alkyl methacrylate in 2-propanol, and preferably the N-vinyl lactam is N-vinyl pyrrolidone and the alkyl methacrylate is n-hexyl methacrylate, and more preferably the copolymer is based on at least 10 mole-percent of N-vinyl pyrrolidone-derived repeat units. Such disinfectant spray bandage composition can be a part of a gas pressurized delivery device capable of in situ forming of an adherent film on viable tissue, such as skin, of a vertebrate animal, wherein the film displays at least 100 percent ultimate elongation, 10 percent reversible elongation, 1.0 MPa maximum stress, and Young's Modulus of less than 100 MPa. And the resulting adherent film exhibits the following properties: (1) an oxygen gas permeability of at least 0.5 cc/100 In$^2$/24 hours at 25° C.; and (2) water-vapor transmission of less than 20 g./100 In$^2$/24 hours @37° C.

A specific aspect of this invention deals with a disinfectant spray bandage composition comprising an alcoholic solution of at least 5 percent w/v of at least one amphiphilic, essentially water-insoluble, segmented/block copolymer of N-vinyl pyrrolidone and n-hexyl methacrylate, having a molecular weight of at least 15 kDa, wherein the alcoholic solution comprises (1) a hemostatic agent; (2) one pain relieving agent, such as benzocain; (3) a bioactive agent selected from the group represented by antimicrobial, antiseptic, anesthetic, analgesic, wound healing, anti-inflammatory, and antiviral agents; and/or (4) a compatible dye, such as D&C Violet No. 2.

Another specific aspect of this invention deals with a tissue protecting spray-on film composition comprising an amphiphilic, film-forming, segmented/block copolymer having a molecular weight of at least 15 kDa derived from at least one water-insoluble alkyl methacrylate and at least one water-soluble monomer selected from the group consisting of N-vinyl pyrrolidone, acrylamide, N-methyl acrylamide, 2-hydroxyethyl methacrylate wherein said copolymer is soluble in one or more water soluble solvent selected from the group represented by ethyl acetate, ethanol, 2-propanol, and acetone, wherein said composition is designed as a disinfectant spray bandage for depositing a flexible-barrier, solid microfilm onto living tissue as in intact or compromised skin, ulcers, or burns, through the combined processes of gas-propelled spray atomization and solvent evaporation, wherein said copolymer is based on at least 10 mole percent of N-vinyl pyrrolidone-derived repeat units and preferably the polyvinyl pyrrolidone component is partially complexed with iodine.

Yet another specific aspect of this invention pertains to a tissue protecting spray-on film composition comprising an amphiphilic, film-forming, segmented/block copolymer having a molecular weight of at least 15 kDa derived from at least one water-insoluble alkyl methacrylate and at least one water-soluble monomer selected from the group consisting of N-vinyl pyrrolidone, acrylamide, N-methyl acrylamide, 2-hydroxyethyl methacrylate wherein said copolymer is soluble in one or more water soluble solvent selected from the group represented by ethyl acetate, ethanol, 2-propanol, and acetone, whereas said composition is designed as a disinfectant spray bandage for depositing a flexible-barrier, solid microfilm onto living tissue as in intact or compromised skin, ulcers, or burns, through the combined processes of gas-propelled spray atomization and solvent evaporation, wherein the alcoholic composition contains trichlosan sodium to yield a clear film comprising at least 0.01 percent w/v of trichlosan sodium.

DETAILED DESCRIPTION OF PREFERRED EMBODIMENTS

This invention deals in general with amphiphilic, segmented/block copolymeric compositions based on at least one water-soluble monomer (or comonomer) and at least one water-insoluble monomer (comonomer). In volatile organic solvent that can be sprayed on compromised or intact tissues to provide a compliant, resilient, stretchable film that is non-water soluble. The spray-on composition and hence, the resulting film may contain active compounds that (1) are capable of reducing pain, as in the case of local anesthetic agents which may include benzocaine (at 0.1 to 5% w/w) and benzethonium chloride (at 0.01 to 0.5% w/w); (2) are antiseptic, such as iodine which may be complexed with the hydrophilic component of the segmented/block copolymer, as is the case with the poly-N-vinyl pyrrolidone segment or block; (3) have bacteriostatic properties, such as trichlosan (or trichlosan sodium); (4) bacteriostatic/ bacteriocidal/antitumor agent, such as dequalinium chloride; (5) have bacteriocidal properties, such as gentamicin; (6) have fungicidal properties, such as miconazole and ketoconazole; (7) are capable of promoting wound healing, such as growth promoters including epidermal growth factor and its peptide analog; and (8) are capable of protecting against sunlight and preventing sunburn, as in the case of UV-B filters [e.g., 2-phenylbenzimadzole sulfonic acids and indoline and its tetrahydroquinoline N-(dicarboalkyloxyvinyl) substituted derivatives], and UV absorbers (e.g., benzazoles).

Another general aspect of this invention deals with a spray-on composition that results in thin films with modulated oxygen permeability and water-vapor transmission rate. This can be achieved by varying the film thickness and the ratio of the hydrophiphilic to hydrophobic component of the copolymer chain. Accordingly, these films can be used in two considerably different applications, such as a (1) wound dressing as preferred alternatives to commercially available, preformed, adhering barrier films, as for example the Opsite Flexigrid® described earlier in the Background of this Invention section; and (2) temporary dressing for split-thickness skin graft donor sites. In effect, as a barrier film and utilizing the moist wound care principle, the amphiphilic film provides a moist healing environment for many types of wounds, including abrasions, blisters, carpet burns, lacerations, poison ivy rash, road rash, and superficial burns. The amphiphilic tissue protecting film can be applied to cuts, burns, blisters, lacerations, or rashes to prevent or minimize scab formation. This will not obstruct the flow of cell migration freely and allow the wound to heal more naturally. A spray-on amphiphilic bandage can provide a highly conformable, thin film cover to compromised skin and presents a preferred alternative to regular bandages that get wet and fall off easily. The spray-on compositions of the present invention can form a clear cover that protects cuts, scrapes, and blisters and helps prevent the formation of calluses. This clear cover is also a compliant and flexible waterproof film that allows the retention of sufficient moisture at the application site and inward diffusion of oxygen, which in turn permit the tissue, as in skin, to breathe and prevent contamination with dirt and germs. The spray-on film for skin application is tougher and more flexible than a regular bandage. It can be applied to large areas, like legs and arms, or hard-to-reach areas. Additionally, the barrier film dressing is permeable to both water vapor and oxygen, but is impermeable to micro-organisms. Once in position, the film provides an effective barrier to external contamination, while producing a moist environment at the surface of the wound by reducing water vapor loss from the exposed tissue. Under these conditions in shallow wounds, scab formation is prevented and epidermal regeneration takes place at an enhanced rate, compared with that which occurs in wounds treated with traditional dry dressings. Hence, the film subject of this invention, may be used in the treatment of scalds, first-or second-degree burns, donor sites, post-operative wounds, minor injuries (including abrasions and lacerations), and for the prevention and treatment of superficial pressure areas. The barrier film dressing may be used also as a temporary dressing for split-thickness, skin graft donor sites. For this application, in addition to achieving smooth and rapid wound healing through protecting the site from dehydration, a strongly bacteriocidal and fungicidal agent (such as tetramethylthiuram disulfide) can be added for protection against potential infection.

For topical skin application and specifically when the solvent of the copolymeric composition is ethanol and/or 2-propanol, the spray-on formulation is considered as a disinfectant one, without adding any antimicrobial agent. The medicated and unmedicated spray-on film may be used as an incise drape.

For oral application, a medicated or unmedicated spray-on film can be used as a (1) hemostatic film in periodontal surgery; (2) protective barrier during periodontal surgical procedures; and (3) protective sealant of dentine, which may also serve as a depot for the controlled delivery of bioactive agents.

A specific aspect of this invention deals with a spray-on composition to yield a conformable, solid, adherent coating (without need to add an adhesive) on biological sites which are (1) of irregular or have acute geometries; (2) difficult to reach; and (3) difficult-to-adhere to tissues, such as wet mucous membranes.

This invention deals generally with a tissue protecting, spray-on film composition comprising an amphiphilic film-forming, segmented/block copolymer derived form at least one water-soluble monomer and at least another water-insoluble monomer wherein said respective film can be formed from a water soluble organic solvent such as 2-propanol, acetone, and ethyl acetate. The film can contain a bioactive agent including those to have antimicrobial, anesthetic, anti-inflammatory, and wound-healing activities.

One primary aspect of this invention deals with a tissue protecting spray-on film composition comprising an amphiphilic, film-forming, segmented/block copolymer having a molecular weight of at least 15 kDa derived from at least one water-insoluble alkyl methacrylate and at least one water-soluble monomer selected from the group consisting of N-vinyl pyrrolidone, acrylamide, N-methyl acrylamide, 2-hydroxyethyl methacrylate wherein said copolymer is soluble in one or more water soluble solvent selected from the group represented by ethyl acetate, ethanol, 2-propanol, and acetone, wherein (1) the said solvent may contain water at more than 0.1 percent of its volume; (2) the segmented/block copolymer may be derived from n-hexyl methacrylate and N-vinyl pyrrolidone; and (3) the segmented/block copolymer may be prepared by the controlled incremental addition of either or both monomers (comonomers) to the polymerization reaction mixture under typical (or traditional) free-radical conditions. An alternative method for preparing the segmented/block copolymer subject of this invention comprises solution or bulk polymerization through controlled/living radical polymerization (CLRP) using $NiBr_2$ $(PPh_3)_2$ as a catalyst and ethyl 2-bromobutyrate as an initiator.

A specific aspect of this invention deals with a tissue protecting spray-on film composition comprising an amphiphilic, film-forming, segmented/block copolymer, having a molecular weight of at least 15 kDa, derived from n-hexyl methacrylate and one or more monomer selected from the group represented by N-vinyl pyrrolidone and 2-hydroxy ethyl methacrylate, acrylamide, and N-methyl acrylamide.

A general aspect of this invention addresses a tissue protecting spray-on film composition comprising an amphiphilic, film-forming, segmented/block copolymer having a molecular weight of at least 15 kDa derived from at least one water-insoluble alkyl methacrylate and at least one water-soluble monomer selected from the group consisting of N-vinyl pyrrolidone, acrylamide, N-methyl acrylamide, 2-hydroxyethyl methacrylate wherein said copolymer is soluble in one or more water soluble solvent selected from the group represented by ethyl acetate, ethanol, 2-propanol, and acetone, wherein the said copolymer is made following a tellurium mediated living radical polymerization (TeRP) using one or more organotellurium compound selected from the group represented by $Ph(CH_3)CH$—Te—$CH_3$, $PHCH_2$—TeMe, Ph—$CH(CH_3)$—Te—$CH_3$, and $(CH_3)_2C(COOEt)$—Te—$CH_3$. wherein Ph=phenyl group and Me=methyl group, and preferably the copolymerization entails the use of dimethyl ditelluride.

Another general aspect of this invention pertains to a tissue protecting spray-on film composition comprising an amphiphilic, film-forming, segmented/block copolymer having a molecular weight of at least 15 kDa derived from at least one water-insoluble alkyl methacrylate and at least one water-soluble monomer selected from the group consisting of N-vinyl pyrrolidone, acrylamide, N-methyl acrylamide, 2-hydroxyethyl methacrylate wherein said copolymer is soluble in one or more water soluble solvent selected from the group represented by ethyl acetate, ethanol, 2-propanol, and acetone, wherein said copolymer comprises an A-B diblock chain structure wherein the A-block is derived from n-hexyl methacrylate and the B-block is derived from a monomer selected from the group represented by N-vinyl pyrrolidone, 2-hydroxyl ethyl methacrylate, acrylamide, and N-methyl acrylamide. Alternatively, the copolymer may be based on an A-B-A triblock chain structure wherein the A-block is derived from a monomer selected from the group represented by N-vinyl pyrrolidone, 2-hydroxyl ethyl methacrylate, acrylamide, and N-methyl acrylamide and the B-block is derived from one or more alkyl methacrylate monomer selected from the group represented by n-hexyl and n-butyl methacrylate or structural isomers thereof. As a second structural alternative, the copolymer may be based on a B-A-B triblock chain structure wherein the A-block is derived from a monomer selected from the group represented by N-vinyl pyrrolidone, 2-hydroxy ethyl methacrylate, acrylamide, and N-methyl acrylamide and the B-block is derived from one or more alkyl methacrylate monomer selected from the group represented by n-hexyl and n-butyl methacrylate, or structural isomers thereof.

Another aspect of this invention pertains to a tissue protecting spray-on film composition comprising an amphiphilic, film-forming, segmented/block copolymer, having a molecular weight of at least 15 kDa in the form of a breatheable, adhering film for protecting compromised skin, wherein said film displays higher oxygen permeability and lower water vapor transmission compared with a Nylon 6 film control at 25° C. and 37° C., respectively.

Another aspect of this invention deals with a tissue protecting spray-on film composition comprising an amphiphilic, film-forming, segmented/block copolymer having a molecular weight of at least 15 kDa derived from at least one water-insoluble alkyl methacrylate and at least one water-soluble monomer selected from the group consisting of N-vinyl pyrrolidone, acrylamide, N-methyl acrylamide, 2-hydroxyethyl methacrylate wherein said copolymer is soluble in one or more water soluble solvent selected from the group represented by ethyl acetate, ethanol, 2-propanol, and acetone, wherein said film functions as a protective barrier for tissues of the buccal cavity, mandibular tissue, and dental varnish.

Another aspect of this invention deals with a tissue protecting spray-on film composition comprising an amphiphilic, film-forming, segmented/block copolymer having a molecular weight of at least 15 kDa derived from at least one water-insoluble alkyl methacrylate and at least one water-soluble monomer selected from the group consisting of N-vinyl pyrrolidone, acrylamide, N-methyl acrylamide, 2-hydroxyethyl methacrylate wherein said copolymer is soluble in one or more water soluble solvent selected from the group represented by ethyl acetate, ethanol, 2-propanol, and acetone, wherein said composition comprises a UVB light-absorbing sunscreen compound for use as a protective film on skin.

A key aspect of this invention deals with a tissue protecting spray-on film composition comprising an amphiphilic, film-forming, segmented/block copolymer having a molecular weight of at least 15 kDa derived from at least one water-insoluble alkyl methacrylate and at least one water-soluble monomer selected from the group consisting of N-vinyl pyrrolidone, acrylamide, N-methyl acrylamide, 2-hydroxyethyl methacrylate wherein said copolymer is soluble in one or more water soluble solvent selected from the group represented by ethyl acetate, ethanol, 2-propanol, and acetone, wherein said composition comprises an antimicrobial agent selected from the group represented by miconazole and ketoconazole for use in treating athletes' foot and nail infection, and/or a biocompatible dye.

A specific aspect of this invention pertains to a tissue protecting spray-on film composition comprising an amphiphilic, film-forming, segmented/block copolymer having a molecular weight of at least 15 kDa derived from at least one water-insoluble alkyl methacrylate and at least one water-soluble monomer selected from the group consisting of N-vinyl pyrrolidone, acrylamide, N-methyl acrylamide, 2-hydroxyethyl methacrylate wherein said copolymer is soluble in one or more water soluble solvent selected from the group represented by ethyl acetate, ethanol, 2-propanol, and acetone, wherein the said composition is used as a disinfectant spray bandage for depositing a flexible-barrier, solid microfilm onto living tissue as in intact or compromised skin, ulcers, or burns, through the combined processes of gas-propelled spray atomization and solvent evaporation.

Another aspect of this invention deals with a disinfectant spray bandage composition comprising an alcoholic solution of at least 5 percent w/v of at least one amphiphilic, essentially water-insoluble segmented/block copolymer having a molecular weight of at least 15 kDa, wherein the alcoholic solution comprises a copolymer of an N-vinyl lactam and an alkyl methacrylate in 2-propanol, and preferably the N-vinyl lactam is N-vinyl pyrrolidone and the alkyl methacrylate is n-hexyl methacrylate, and more preferably the copolymer is based on at least 10 mole-percent of N-vinyl pyrrolidone-derived repeat units. Such disinfectant spray bandage composition can be a part of a gas pressurized delivery device capable of in situ forming of an adherent film on viable tissue, such as skin of a vertebrate animal, wherein the film displays at least 100 percent ultimate elongation, 10 percent reversible elongation, 1.0 MPa maximum stress, and Young's Modulus of less than 100 MPa. And the resulting adherent film exhibits the following properties: (1) an oxygen gas permeability of at least 0.5 cc/100 In$^2$/24 hours at 25° C.; and (2) water-vapor transmission of less than 20 g./100 In$^2$/24 hours @37° C.

A specific aspect of this invention deals with a disinfectant spray bandage composition comprising an alcoholic solution of at least 5 percent w/v of at least one amphiphilic, essentially water-insoluble, segmented/block copolymer of N-vinyl pyrrolidone and n-hexyl methacrylate, having a molecular weight of at least 15 kDa, wherein the alcoholic solution comprises (1) a hemostatic agent; (2) one pain relieving agent, such as benzocain; (3) a bioactive agent selected from the group represented by antimicrobial, antiseptic, anesthetic, analgesic, wound healing, anti-inflammatory, and antiviral agents; and/or (4) a compatible dye, such as D&C Violet No. 2.

Another specific aspect of this invention deals with a tissue protecting spray-on film composition comprising an amphiphilic, film-forming, segmented/block copolymer having a molecular weight of at least 15 kDa derived from at least one water-insoluble alkyl methacrylate and at least one water-soluble monomer selected from the group consisting of N-vinyl pyrrolidone, acrylamide, N-methyl acrylamide, 2-hydroxyethyl methacrylate wherein said copolymer is soluble in one or more water soluble solvent selected from the group represented by ethyl acetate, ethanol, 2-propanol, and acetone, wherein said composition is designed as a disinfectant spray bandage for depositing a flexible-barrier, solid microfilm onto living tissue as in intact or compromised skin, ulcers, or burns, through the combined processes of gas-propelled spray atomization and solvent evaporation, wherein said copolymer is based on at least 10 mole percent of N-vinyl pyrrolidone-derived repeat units and preferably the polyvinyl pyrrolidone component is partially complexed with iodine.

Yet another specific aspect of this invention pertains to a tissue protecting spray-on film composition comprising an amphiphilic, film-forming, segmented/block copolymer having a molecular weight of at least 15 kDa derived from at least one water-insoluble alkyl methacrylate and at least one water-soluble monomer selected from the group consisting of N-vinyl pyrrolidone, acrylamide, N-methyl acrylamide, 2-hydroxyethyl methacrylate wherein said copolymer is soluble in one or more water soluble solvent selected from the group represented by ethyl acetate, ethanol, 2-propanol, and acetone, whereas said composition is designed as a disinfectant spray bandage for depositing a flexible-barrier, solid microfilm onto living tissue as in intact or compromised skin, ulcers, or burns, through the combined processes of gas-propelled spray atomization and solvent evaporation, wherein the alcoholic composition contains trichlosan sodium to yield a clear film comprising at least 0.01 percent w/v of trichlosan sodium.

Further illustrations of the present invention are provided by the following examples:

EXAMPLE 1

General Method of Preparation and Characterization of Segmented/Block Copolymers of Alkyl Methacrylate/N-Vinyl Pyrrolidone Copolymer Using Classical Free-radical Conditions The copolymerization was carried out in two steps. In the first step, N-vinyl pyrrolidone, a small amount of an alkyl methacrylate, and a catalytic amount of a free-radical initiator were mixed under an oxygen-free environment in a mechanically stirred reaction flask. The mixture was heated for about 30 minutes at 65° C.-85° C. to allow partial polymerization of the comonomers. At this point, the second step commenced by adding a solution of alkyl methacrylate and an additional amount of the free-radical initiator over a long period of time. After completing the addition of the second charge, the reaction was continued for an additional 30 minutes. When the copolymer formation practically ceased, as determined by gel permeation chromatographic analysis of unreacted comonomer, the reaction was terminated and the copolymer was precipitated in water, rinsed with dry ice-cooled methanol. Further purification of the copolymer was accomplished by precipitating its chloroform solution into dry ice-cooled methanol. The purified product was then filtered and dried at room temperature in a laminar flow hood and then at 40° C. under reduced pressure until a constant weight is attained.

The purified copolymer was characterized for molecular weight (GPC), identify (IR), and composition (NMR and elemental nitrogen analysis).

EXAMPLE 2

Copolymerization of 25/75 N-Vinyl Pyrrolidone (NVP)/n-Hexyl Methacrylate (HMA) to Produce Segmented/Block Copolymer SC-I The preparation of SC-I, its isolation, purification, and characterization were conducted following the general methods described in Example 1. More specific details are provided below.

The first charge was based on an N-vinyl-2-pyrrolidone (NVP) rich comonomer mixture. Thus NVP (0.163 mole), n-hexyl methacrylate (HMA) (0.0654 mole), 1,4-dioxane (49 mL) and 2-2' Azo-bis-isobutyronitrile (2.31 mmole) were mixed/dissolved. The mixture was sparged with nitrogen for two minutes, added to a flask that was kept under a positive nitrogen pressure, and mechanically stirred at 60 RPM in a 65° C. silicon oil bath for a total of 30 minutes. For the second charge, HMA (0.422 mole), 1,4-dioxane (49 mL), and 2-2' Azo-bis-isobutyronitrile (2.31 mmole) were mixed/dissolved. The mixture was sparged with nitrogen for 2 minutes and added to the product of the first charge at a constant flow rate (controlled by a peristaltic pump) over a period of 17 hours. The reaction was allowed to continue at 65° C. for an additional 30 minutes.

The polymer was precipitated in ice water in a blender, filtered using a filter funnel, blended in −60° C. methanol, filtered and dried under reduced pressure at room temperature. It was dissolved as a 20-weight-percent solution in chloroform, precipitated in −60° C. methanol, filtered, dissolved in chloroform, poured onto a Teflon tray and dried to constant weight under reduced pressure at 45° C.

The purified copolymer was shown (1) to be soluble in 2-propanol, but not water-soluble; (2) by GPC (using dichloromethane, DCM, as a solvent) to have an $M_n$=54.6 kDa, $M_w$=99.1 kDa, and PDI=1.82: and (3) by elemental nitrogen analysis to be based on 18.4/81.6 (molar) NVP/HMA. The infrared (IR) and NMR data were consistent with the elemental analysis data.

EXAMPLE 3

Copolymerization of 30/70 N-Vinyl Pyrrolidone (NVP)/n-Hexyl Methacrylate (HMA) to Produce Segmented/Block Copolymer SC-II The preparation of SC-II, its isolation, purification, and characterization were conducted following the general methods described in Example 1. More specific details are provided below.

The first charge was based on an N-vinyl-2-pyrrolidone (NVP) rich comonomer mixture. Thus NVP (0.189 mole), n-hexyl methacrylate (HMA) (0.0633 mole), 1,4-dioxane (47 mL) and 2-2' Azo-bis-isobutyronitrile (2.19 mmole) were mixed/dissolved. The mixture was sparged with nitrogen for two minutes, added to a flask that was kept under a positive nitrogen pressure, and mechanically stirred at 60 RPM in a 65° C. silicon oil bath for a total of 30 minutes. For the second charge, HMA (0.377 mole), 1,4-dioxane (47 mL), and 2-2' Azo-bis-isobutyronitrile (2.19 mmole) were mixed/dissolved. The mixture was sparged with nitrogen for 2 minutes and added to the product of the first charge at a constant flow rate (controlled by a peristaltic pump) over a period of 16 hours. The reaction was allowed to continue at 65° C. for an additional 30 minutes.

The polymer was precipitated in ice water in a blender, filtered using a filter funnel, blended in −60° C. methanol, filtered and dried under reduced pressure at room temperature. It was dissolved as a 20-weight-percent solution in chloroform, precipitated in −60° C. methanol, poured onto a Teflon tray, and dried to constant weight.

The purified copolymer was shown (1) to be soluble in 2-propanol, but not water-soluble; (2) by GPC (in DCM) to have an $M_n$=48.0 kDa, $M_w$=111.4 kDa, and PDI=2.32: and (3) by elemental nitrogen analysis to be based on 24.8/75.2 (molar) NVP/HMA. The IR and NMR data were consistent with the elemental analysis data.

EXAMPLE 4

Copolymerization of 35/65 N-Vinyl Pyrrolidone (NVP)/n-Hexyl Methacrylate (HMA) to Produce Segmented/Block Copolymer SC-III The preparation of SC-III, its isolation, purification, and characterization were conducted following the general methods described in Example 1. More specific details are provided below.

The first charge was based on an N-vinyl-2-pyrrolidone (NVP)-rich comonomer mixture. Thus NVP (0.226 mole), n-hexyl methacrylate (HMA) (0.0647 mole), 1,4-dioxane (47 mL) and 2-2'Azo-bis-isobutyronitrile (2.20 mmole) were mixed/dissolved. The mixture was sparged with nitrogen for two minutes, added to a flask that was kept under a positive nitrogen pressure, and mechanically stirred at 60 RPM in a 65° C. silicon oil bath for a total of 30 minutes. For the second charge, HMA (0.355 mole), 1,4-dioxane (47 mL), and 2-2' Azo-bis-isobutyronitrile (2.20 mmole) were mixed/dissolved. The mixture was sparged with nitrogen for 2 minutes and added to the product of the first charge at a constant flow rate (controlled by a peristaltic pump) over a period of 14.5 hours. The reaction was allowed to continue at 65° C. for an additional 30 minutes.

The polymer was precipitated in ice water in a blender, filtered using a filter funnel, blended in −60° C. methanol, filtered and dried under reduced pressure at room temperature. It was dissolved as a 20-weight-percent solution in chloroform, precipitated in −60° C. methanol, poured onto a Teflon tray, and dried to constant weight. This precipitation was repeated once more to give an "extra pure" polymer.

The purified copolymer was shown (1) to be soluble in 2-propanol, but not water-soluble; (2) by GPC (in DCM) to have an $M_n$=41.7 kDa, $M_2$=101.1 kDa, and PDI=2.42: and (3) by elemental nitrogen analysis to be based on 25.8/74.2 (molar) NVP/HMA. The IR and NMR data were consistent with the elemental analysis data.

EXAMPLE 5

Film Formation-General Method

The desired amount of SC-I, SC-II, or SC-III, from Examples 2, 3 or 4, was dissolved in 2-propanol to yield a solution having a solid content between 10 and 25 percent (w/v), depending on the desired film thickness. The polymer solution was cast on a flat Teflon sheet and thickness was then adjusted with a horizontally rolling draw rod. The film was allowed to dry in a laminar flow hood. The drying time was predetermined in a pilot experiment to insure that the drying process resulted in a constant film weight.

These films were used to test their tensile properties, oxygen, permeability and water vapor transmission.

EXAMPLE 6

Measurement of Film Tensile Properties

Film of SC-I to SC-III from Examples 2 to 4 were prepared as described in Example 5. The tensile properties were measured using an MTX MiniBionix Universal Tester, Model 858, at a strain rate of 1 mm/sec. The tensile properties of the different films (about 0.1 mm thick) are summarized in Table I.

TABLE I

Tensile Properties of Films Made of Copolymers SC-I, SC-II, and SC-III

| Copolymer | Mole % NVP (Theoretical) | Mole % NVP (Actual) | Max Load (N) | Max Stress (MPa) | % Elongation | Young's Modulus (MPa) |
|---|---|---|---|---|---|---|
| SC-I | 25 | 18.4 | 0.71 | 1.5 | 317 | 6 |
| SC-II | 30 | 24.8 | 1.30 | 3.1 | 184 | 38 |
| SC-III | 35 | 25.8 | 1.51 | 3.0 | 113 | 37 |

EXAMPLE 7

Measurement of Film Oxygen Permeability

Films of SC-I to SC-III from Examples 2 to 4 were prepared as described in Example 5. The oxygen permeability (OP) on the individual films was measured on a Mocon Oxtran 2/20 (ST system) at 35° C., according to ASTM Method Number D-3985-02. Oxygen permeability data of the different films are summarized in Table II.

TABLE II

Oxygen Permeability Data[a]

| Film | Polymer No. (Example No.) | Film Thickness (micron) | OP g/m$^2$/d |
|---|---|---|---|
| F-I-b | SC-I (2) | | |
| F-II-b | SC-II (3) | | |
| F-III-b | SC-III (4) | | |

[a]ASTM Method Number: D 3985-02

EXAMPLE 8

Measurement of Film Water Vapor Transmission (WVT)

Films of SC-I to SC-III from Examples 2 to 4 were prepared as described in Example 5. The WVT of the individual films was measured using a Mocon Permatran-W600 at 37° C. and RH=100%, according to ASTM Method Number F-1770-97. The oxygen permeability data of the different films are summarized in Table III.

TABLE III

Water-Vapor Transmission Data[a]

| Film | Polymer No. (Example No.) | Film Thickness (micron) | WVT g/m$^2$/d |
|---|---|---|---|
| F-I-a | SC-I (2) | 35 | 6.67 |
| F-II-a | SC-II (3) | 55 | 6.61 |
| F-III-a | SC-III (4) | 55 | 6.22 |

[a]ASTM Method Number: F-1770-97

Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that aspects of the various embodiments may be interchanged in whole or in part. Therefore, the spirit and scope of the appended claims should not be limited to descriptions and examples herein.

What is claimed is:

1. A tissue protecting, spray-on film composition consisting essentially of an amphiphilic, segmented/block copolymer having A-B diblock chain structure, wherein the A-block is derived from at least one water-insoluble monomer comprising an alkyl methacrylate, and wherein the B-block is derived from at least one water-soluble monomer comprising N-vinyl pyrrolidone, wherein said copolymer has a molecular weight of at least 15 kDa and is dissolved in at least one water soluble solvent selected from the group consisting of ethyl acetate: ethanol, 2-propanol, and acetone.

2. A tissue protecting, spray-on film composition as in claim 1 wherein the water soluble solvent further comprises at least about 0.1% by volume of water.

3. A tissue protecting, spray-on film composition as in claim 1 wherein the alkyl methacrylate comprises n-hexyl methacrylate.

4. A tissue protecting, spray-on film composition as in claim 1 consisting essentially of an amphiphilic, segmented/block copolymer having A-B-A triblock chain structure, wherein the A-blocks are derived from N-vinyl pyrrolidone and the B-block is derived from at least one alkyl methacrylate monomer selected from the group consisting of n-hexyl methacrylate and n-butyl methacrylate.

5. A tissue protecting, spray-on film composition as in claim 1 consisting essentially of an amphiphilic, segmented/block copolymer having B-A-B triblock chain structure wherein the A-block is derived from N vinyl pyrrolidone and the B-blocks are derived from at least one alkyl methacrylate monomer selected from the group consisting of n-hexyl methacrylate and n-butyl methacrylate.

6. A tissue protecting, spray-on film composition as in claim 1 wherein the film functions as a protective barrier for tissues of the buccal cavity and mandibular tissue.

7. A tissue protecting, spray-on film composition as in claim 1 wherein the film functions as a dental varnish.

8. A tissue protecting, spray-on film composition as in claim 1 further comprising a UVB light-absorbing sunscreen compound for use as a protective film on skin.

9. A tissue protecting, spray-on film composition as in claim 1 further comprising an antimicrobial agent selected from the group consisting of miconazole and ketoconazole, for use in treating athletes' foot and nail infections.

10. A tissue protecting, spray-on film composition as in claim 1 further comprising a biocompatible dye.

11. A tissue protecting, spray-on film composition as in claim 1 wherein the water soluble solvent comprises 2-propanol and wherein the film is formed through the combined processes of gas-propelled spray atomization and solvent evaporation.

12. A tissue protecting, spray-on film composition as in claim 1 wherein the segmented/block copolymer is made by a method comprising controlled, incremental addition of at least one of the monomers to a polymerization reaction mixture under typical free-radical conditions.

* * * * *